United States Patent
Groziak (10) Patent No.: US 6,248,305 B1
(45) Date of Patent: Jun. 19, 2001

(54) BORON HETEROCYCLE STEROID MIMICS AND ASSOCIATED PHARMACEUTICAL COMPOSITIONS AND METHODS OF USE

(75) Inventor: Michael P. Groziak, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/490,601

(22) Filed: Jan. 25, 2000

Related U.S. Application Data (63) Continuation-in-part of application No. 09/236,948, filed on Jan. 25, 1999, now Pat. No. 6,083,936.

(51) Int. Cl.[7] .................. A61K 51/00; A61K 31/69; A61B 5/055; C07F 5/04; C07F 5/02
(52) U.S. Cl. .................. 424/1.61; 424/9.3; 514/64; 558/289; 562/882
(58) Field of Search .................. 424/9.3, 1.61; 514/64; 558/289; 562/882

(56) References Cited

U.S. PATENT DOCUMENTS

| | | |
|---|---|---|
| 5,144,026 | 9/1992 | Gabel . |
| 5,362,732 | 11/1994 | Spielvogel et al. . |
| 5,599,796 | 2/1997 | Schinazi et al. . |
| 5,612,017 | 3/1997 | Miura et al. . |
| 5,648,532 | 7/1997 | Hawthorne et al. . |
| 5,872,224 * | 2/1999 | Stolowitz et al. ............ 530/396.1 |
| 6,037,490 * | 3/2000 | Kabalka et al. ............ 562/7 |
| 6,074,625 * | 6/2000 | Hawthorne et al. ............ 424/1.11 |
| 6,083,936 * | 7/2000 | Groziak ............ 514/64 |
| 6,086,837 * | 7/2000 | Cowan et al. ............ 423/294 |
| 6,117,852 * | 9/2000 | Chou ............ 514/64 |
| 6,180,766 * | 1/2001 | Schinazi et al. ............ 536/22.1 |

OTHER PUBLICATIONS

Bailey et al. (1980), "Boron–Containing Antibacterial Agents: Effects on Growth and Morphology of Bacteria Under Various Culture Conditions", *Antimicrobial Agents and Chem.* 17(4):549–553.

Baldock et al. (1996), "A Mechanism of Drug Action Revealed by Structural Studies of Enoyl Reductase," *Science* 274:2107–2110.

Barsony et al. (1995), "Development of a Biologically Active Fluorescent–labeled Calcitriol and its Use to Study Hormone Binding to the Vitamin D Receptor," *Analytical Biochem.* 229:68–79;

French et al. (1993), "A Synthesis of 7α–substituted Estradiols: Synthesis and Biological Evaluation of a 7α–pentyl-substituted Bodipy Fluorescent Conjugate and a Fluorine–18–labeled 7α–pentylestradiol Analog," *Steroids* 58: 157–169.

Grassberger et al. (1984), "Preparation and Antibacterial Activities of New 1,2,–Diazaborine Derivatives and Analogues," *J. Med. Chem.* 27:947–953.

Groziak et al. (1994), "Boron Heterocycles Bearing a Peripheral Resemblance to Naturally–Occurring Purines: Design, Syntheses, Structures and Properties," *J. Am Chem. Soc.* 116: 7597–7605.

Groziak et al. (1997), "Planar Boron Heterocycles with Nucleic Acid–Like Hydrogen–Bonding Motifs," *J. Am. Chem. Soc.* 119: 7817–7826.

Kabalka et al. (1997), "The Role of Boron MRI in Boron Neutron Capture Therapy," *J. Neuro–Oncol.* 33: 153–161.

Kabalka et al. (1988), "Boron–11 MRI and MRS of Intact Animals Infused With a Boron Neutron Capture Agent," *Magnetic Resonan. Med.* 8: 231–237.

Robinson et al. (1998), "A 2–Alkyl Substituted 2,3,1–Benzodiazaborane," *J. Acta Crystallogr.* C54: 71–73.

Sweet (1981), "Boron Estrogens: Synthesis, Biochemical and Biological Testing of Estrone and Estradiol–17β, 3–carboranylmethyl Ethers," *Steroids* 37:223–238.

Wellmann et al. (1991), "Synthesis and Biological Behavior of a Boronated Analogue of the Antiestrogen U 23, 469–m," *Z. Naturforsch* [C] 46:252–256.

Robinson et al. (1999), "A Boron–Containing Estrogen Mimic," *Acta Cryst.* C55:1701–1704.

Groziak, "Boron Heterocycle–Based Estrogen Mimics," Abstract PO–335, presented at the 17th International Congress of Heterocyclic Chemistry (Institute of Organic Chemistry, Vienna Institute of Technology) Aug. 1–6, 1999.

Davis et al. (1998), "Synthesis and Evaluation of Benzodiazaborine Compounds Against *M. Tuberculosis* $H_{37}R_v$ In Vitro," *Bioorganic & Medicinal Chemistry Letters* 8:843–846.

Robinson et al. (1999), "A Boron–Containing Estrogen Mimic," *Acta Crystallogr., Sect. C: Cryst. Struct. Commun.* C55(10): 1701–1704 (abstract only).

* cited by examiner

*Primary Examiner*—Deborah C. Lambkin
(74) *Attorney, Agent, or Firm*—Dianne E. Reed; Reed & Associates (57) ABSTRACT

Boron heterocycle steroid mimics are provided that are useful as pharmaceutical agents, particularly in the treatment of estrogen-dependent disorders such as estrogen-dependent cancers. The compounds are also useful in diagnostic techniques such as magnetic resonance imaging (MRI) and magnetic resonance spectroscopy (MRS), in boron neutron capture therapy, and in fluorescence emission-based modalities. Pharmaceutical formulations and methods of using the novel compounds are provided as well.

36 Claims, 1 Drawing Sheet

FIGURE 1

BORON HETEROCYCLE STEROID MIMICS AND ASSOCIATED PHARMACEUTICAL COMPOSITIONS AND METHODS OF USE

CROSS-REFERENCE TO RELATED APPLICATIONS

This is a continuation-in-part of U.S. patent application Ser. No. 09/236,948, filed Jan. 25, 1999, Pat. No. 6,083,936.

TECHNICAL FIELD

The present invention relates generally to pharmaceuticals, and more particularly relates to novel pharmaceutical agents in the form of boron heterocycle steroid mimics. The invention additionally relates to pharmaceutical compositions containing a compound of the invention, and to methods for using the novel compounds as therapeutic and diagnostic agents.

BACKGROUND

Despite continuing research on breast cancer chemotherapy, almost all of the chemotherapeutic agents currently used to treat breast cancer still fall into just two categories: modified steroids (framework A); and compounds related to diethylstilbestrol (framework B).

Framework "A":
Examples of "A"-Type Chemotherapeutic Agents:

4-Hydroxyandrostenedione
(4-OHA, Formestane)

Medroxyprogesterone Acetate

Megestrol Acetate

Promegestone

Danazol

Framework "B":

Examples of "B"-Type Chemotherapeutic Agents:

Tamoxifen

-continued

Idoxifene

The best agents currently in clinical use are not significantly more effective than the 30-year-old antiestrogen tamoxifen (Nolvadex®), shown above, or the first generation aromatase inhibitors. Furthermore, toxic side effects and the emergence of drug resistance continue to be problematic. It is accordingly critical that new molecular platforms be developed for the development of new, highly effective agents useful in breast cancer chemotherapy. The present invention is addressed to this timely and urgent need in the art.

The invention provides an entirely new class of compounds that are structural mimics of the two principal natural estrogens, estradiol and estrone, but are otherwise unlike any pharmaceutical agents known to date. The novel compounds are boron heterocycles that effectively inhibit human breast cancer cell growth either by blocking the estrogen-receptor-dependent growth signal, by inhibiting an estrogen-producing enzyme, or both. The compounds are also advantageous insofar as the boron atom within the molecular structure enables use in $^{11}$B nuclear magnetic resonance and magnetic resonance imaging. The novel boron-based estrogen mimics are additionally useful in boron neutron capture therapy for treating a variety of tumor types, including breast cancer. Further, those compounds of the invention that are fluorescent can be used in diagnostic procedures involving fluorescence emission spectroscopy, as will be appreciated by those skilled in the art.

Carbone derivatives of estrogens are described in Sweet (1981), "Boron Estrogens: Synthesis, Biochemical and Biological Testing of Estrone and Estradiol-17β, 3-carboranylmethyl Ethers," *Steroids* 37:223–238, where the derivative was shown to have a low affinity for the estrogen receptor of only 0.5 compared with a value of 100 for estradiol-17β. Wellmann et al. (1991), "Synthesis and Biological Behavior of a Boronated Analogue of the Antiestrogen U 23,469-m," *Z. Naturforsch* [C] 46:252–256, concludes that the boronated analogue has a large, nonspecific uptake in ZR 75-1 breast cancer cells, but does not accumulate at high enough level, in cells to have any therapeutic effect following thermal neutron irradiation. There is some description in the literature concerning boron heterocycles as potential pharmaceutical agents. For example, Groziak et al. (1994), "Boron Heterocycles Bearing a Peripheral Resemblance to Naturally-Occurring Purines: Design, Syntheses, Structures and Properties," *J. Am. Chem. Soc.* 116:7597–7605, discloses boron-containing purine-like heterocycles as potentially useful bioactive agents. Groziak et al. (1997), "Planar Boron Heterocycles with Nucleic Acid-Like Hydrogen-Bonding Motifs," *J. Am. Chem. Soc.* 119:7817–7826, pertains to similar boron-containing compounds. Robinson et al. (1998), "A 2-Alkyl Substituted 2,3,1-Benzodiazaborane," *J. Acta Crystallogr.* C54:71–73, relates structural information pertaining to a benzodiazaborane, specifically 1,2-dihydro-1-hydroxy-2-methyl-2,3,1-benzodiazaborine. Still other references describe 2,3,1-benzodiazaborines as antibacterial agents; see, e.g., Baldock et al. (1996), "A Mechanism of Drug Action Revealed by Structural Studies of Enoyl Reductase," *Science* 274:2107–2110; Grassberger et al. (1984), "Preparation and Antibacterial Activities of New 1,2,3-Diazaborine Derivatives and Analogs," *J. Med. Chem.* 27:947–953; and Bailey et al., "Boron-Containing Antibacterial Agents: Effects on Growth and Morphology of Bacteria Under Various Culture Conditions," *J. Antimicrob. Agents Chemother.* 17:549–553.

Boron-containing compounds have been used in boron neutron capture therapy (BNCT). BNCT is an anti-cancer bimodal radiation therapy utilizing a radiosensitizing compound that contains a stable boron-10 isotope and nonionizing neutron radiation. The patient is first administered the boron-containing compound that is preferably although not necessarily enriched in boron-10 isotope. In the second step, the tumor area is irradiated with thermal neutrons. Some of the neutrons are captured by boron-10 in the tumor and a nuclear reaction occurs that results in the production of helium nuclei (α-particle), lithium nuclei, and about 100 million times more energy than the initial irradiated energy. The generated energy destroys malignant cells containing the boron compounds. Selectivity is thus achieved through the use of compounds which accumulate primarily in malignant cells and/or by aiming the neutron beam at the tumor mass which contains the boron carrier. U.S. Pat. No. 5,599,796 to Schinazi et al. describes boron-containing anti-sense oligonucleotides for BNCT targeting urogenital cancer cells, while U.S. Pat. No. 5,362,732 to Spielvogel et al. describes boronate purine and pyrimidine bases and phosphate esters for use in BNCT. U.S. Pat. No. 5,612,017 to Miura et al. describes a dimeric halogenated sulfidohydroborane compound for BNCT, and U.S. Pat. No. 5,648,532 to Hawthorne et al. describes boron salts encapsulated with liposomes for use in BNCT.

The concentration of boron-10 within the tissues of patients to whom boron-containing compounds have been administered has been estimated by extrapolation from the concentration of boron-10 in blood and tissue samples. These indirect extrapolations, however, are approximate, and a more accurate method of determining the concentration and distribution of boron-10 in a patient being prepared for BNCT is needed. Multinuclear magnetic resonance imaging (MRI) and spectroscopy (MRS) are potentially valuable for evaluation of BNCT agents since boron-10 and boron-11 are magnetically active. Kabalka et al. (1988), "Boron-11 MRI and MRS of Intact Animals Infused With a Boron Neutron Capture Agent," *Magnetic Resonan. Med.* 8: 231–237, describe the use of cesium μ-disulfido-bis (undecahydro-closo-dodecaborate) in imaging experiments with rats, while the use of the compound in imaging mammals is described in Kabalka et al. (1997), *J. Neuro-Oncol.* 33: 153–161. In addition, French et al. (1993), "A Synthesis of 7α-substituted Estradiols: Synthesis and Biological Evaluation of a 7α-pentyl-substituted Bodipy Fluorescent Conjugate and a Fluorine-18-labeled 7α-pentylestradiol Analog," *Steroids* 58:157–169, describes the conjugation of a BODIPY fluorophore with an estradiol as a fluorescent probe for the estrogen receptor, while Bolger et al. (1998), "Rapid Screening of Environmental Chemicals for Estrogen Receptor Binding Capacity," *Environ. Health Perspect.* 106 (9):551–557, describe HTS (high throughput screening) of fluorescence-based estrogen receptor ligands. Barsony et al.

(1995), "Development of a Biologically Active Fluorescent-labeled Calcitriol and its Use to Study Hormone Binding to the Vitamin D Receptor," disclose the conjugation of a BODIPY fluorophore to calcitriol derivatives as a fluorescent probe for vitamin D receptor.

The use of boron heterocycles as provided herein, however, is believed to be new and completely unsuggested by the art. That is, no art of which applicants are aware discloses the boron heterocycle steroid mimics for the treatment of cancer or for any other purpose, either therapeutic or diagnostic.

SUMMARY OF THE INVENTION

Accordingly, it is a primary object of the invention to address the above-described need in the art by providing novel compounds useful as chemotherapeutic agents, particularly in the treatment of breast cancer.

It is another object of the invention to provide such compounds in the form of boron heterocycle steroid mimics.

It is an additional object of the invention to provide pharmaceutical compositions containing one or more of the novel compounds as an active agent.

It is still another object of the invention to provide a method for treating an estrogen-dependent disorder by administering a compound of the invention to an individual suffering from such a disorder.

It is yet another object of the invention to provide such a method wherein the estrogen-dependent disorder is breast cancer.

It is a further object of the invention to provide a method for using the present compounds in diagnostic techniques, such as magnetic resonance imaging (MRI) and magnetic resonance spectroscopy (MRS).

It is still a further object of the invention to provide a method for using a compound of the invention in boron neutron capture therapy to treat a cancer patient.

It is yet a further object of the invention to provide a method for using a compound of the invention in fluorescence emission-based modalities.

Additional objects, advantages and novel features of the invention will be set forth in part in the description which follows, and in part will become apparent to those skilled in the art upon examination of the following, or may be learned by practice of the invention.

In one embodiment of the invention, then, a novel compound is provided having the structural formula (I)

In one embodiment of the invention, then, a novel compound is provided having the structural having the structural formula (I)

(I)

wherein:

a and b represent optional double bonds;

$R^1$ is H, carbonyl, methylene or mono(lower alkyl)-substituted methylene, wherein, when carbonyl, methylene or mono(lower alkyl)-substituted methylene, $R^1$ is covalently bound to an atom contained within R;

$R^2$ is selected from the group consisting of H, lower alkyl, lower acyl, phenyl, benzyl, —C(O)-aryl and —SO$_2$NH$_2$;

$R^3$ is H or lower alkyl;

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein $R^9$ and $R^{10}$ are independently H or lower alkyl;

$R^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein $R^9$ and $R^{10}$ are independently H or lower alkyl;

$R^6$ is selected from the group consisting of H, hydroxyl, —OR$^{11}$ and —SR$^{11}$ wherein $R^{11}$ is, H, lower alkyl, lower acyl or aryl;

R is hydrocarbyl, substituted hydrocarbyl, heteroatom-containing hydrocarbyl or substituted heteroatom-containing hydrocarbyl;

X is N, CH or CR$^{12}$ wherein $R^{12}$ is alkyl, aryl, —O-alkyl, —O-aryl, —S-alkyl or —S-aryl;

or is a pharmaceutically acceptable salt or ester thereof.

In another embodiment of the invention, pharmaceutical compositions are provided comprising a compound of the invention in combination with a pharmaceutically acceptable carrier. For those compounds that are orally active, oral formulations such as tablets, capsules, and the like are preferred. However, the invention also encompasses other types of formulations suited to various modes of administration, and includes, for example, injectable solutions, powders, suppositories, sprays, creams, ointments and the like.

In additional embodiments of the invention, methods of using the novel compounds are provided. A primary use of the compounds of the invention is in the treatment of cancer, particularly estrogen-dependent cancers such as breast and uterine cancer. The compounds are also useful to treat other estrogen-dependent disorders such as benign breast disease, endometriosis, osteoporosis, and the like. The compounds are additionally useful as diagnostic agents, particularly in MRI and MRS, in boron neutron capture therapy, and in fluorescence emission-based modalities.

DETAILED DESCRIPTION OF THE INVENTION

Definitions and Nomenclature

Before the present compounds, compositions and methods are disclosed and described, it is to be understood that this invention is not limited to specific molecular structures, methods of synthesis, pharmaceutical compositions, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a novel compound" in a composition means that more than one of the novel compounds can be present in the composition, reference to "a pharmaceutically acceptable carrier" includes combinations of such carriers, and the like. Similarly, reference to "a substituent" as in a compound substituted with "a substituent" includes the possibility of substitution with more than one substituent, wherein the substituents may be the same or different.

In this specification and in the claims which follow, reference will be made to a number of terms which shall be defined to have the following meanings:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution. Similarly, the phrase an "optionally present" double bond as indicated by a dotted line ----- in the chemical formulae herein means that a double bond may or may not be present, and, if absent, a single bond is indicated.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms.

Similarly, the term "alkyl thio" as used herein intends an alkyl group bound through a single, terminal thioether linkage; that is, an "alkyl thio" group may be represented as —S-alkyl where alkyl is as defined above. A "lower alkyl thio" group intends an alkyl thio group containing one to six, more preferably one to four, carbon atoms.

The term "acyl" is used in its conventional sense to refer to a substituent alkyl-C—(O)—wherein alkyl is as defined above. The term "lower acyl" refers to an acyl group wherein the alkyl moiety of the group contains one to six, more preferably one to four, carbon atoms.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "amino" is used herein to refer to the group —$NZ^1Z^2$, where each of $Z^1$ and $Z^2$ is independently selected from the group consisting of hydrido and optionally substituted alkyl, alkenyl, alkynyl, aryl, aralkyl, alkaryl and heterocyclic.

The term "thio" is used herein to refer to the group —$SZ^1$, where $Z^1$ is selected from the group consisting of hydrido and optionally substituted alkyl, alkenyl, alkynyl, aryl, aralkyl, alkaryl and heterocyclic.

The term "available" carbon or nitrogen atom refers to a carbon or nitrogen atom which is covalently bonded to one or more hydrogen atoms which can be replaced by a designated substituent without disrupting or destabilizing the remaining structure of the molecule.

By the terms "effective amount" or "pharmaceutically effective amount" of an agent as provided herein are meant a nontoxic but sufficient amount of the agent to provide the desired effect. As will be pointed out below, the exact amount required will vary from subject to subject, depending on the species, age, and general condition of the subject, the severity of the condition being treated, and the particular active agent and mode of administration, and the like. Thus, it is not possible to specify an exact "effective amount." However, an appropriate "effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected anti-estrogenic agent without causing any undesirable biological effects or interacting in a deleterious manner with any of the other components of the pharmaceutical composition in which it is contained. Similarly, a "pharmaceutically acceptable" salt or a "pharmaceutically acceptable" ester of a novel compound as provided herein is a salt or ester which is not biologically or otherwise undesirable.

In describing the location of groups and substituents, the above numbering systems will be employed, to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β," denoted by a bold line, indicates that the group at the position in question is above the general plane of the molecule as drawn.

In addition, the five- and six-membered rings of the steroid molecule are often designated A, B, C and D as shown.

The Novel Compounds

In one embodiment, the invention is directed to novel compounds having the structural formula (I)

wherein a and b represent optional double bonds, and in a preferred embodiment are present as double bonds, and $R^1$ through $R^6$, X and R are defined as follows.

$R^1$ is H, carbonyl, methylene or mono(lower alkyl)-substituted methylene, wherein, when carbonyl, methylene or mono(lower alkyl)-substituted methylene, $R^1$ is directly and covalently bound to an atom contained within R. Preferably, $R^1$ is selected from the group consisting of H, carbonyl and methylene. It is also preferred that $R^1$ is H or methylene.

$R^2$ is selected from the group consisting of H, lower alkyl, lower acyl, phenyl, benzyl, —C(O)-aryl and —SO$_2$NH$_2$. Preferably, $R^2$ is H or a hydroxyl-protecting group, and, most preferably, $R^2$ is H.

$R^3$ is H or lower alkyl, preferably H.

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein $R^9$ and $R^{10}$ are independently H or lower alkyl. Preferably, $R^4$ is H.

$R^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein $R^9$ and $R^{10}$ are independently H or lower alkyl. Preferably, $R^5$ is H.

$R^6$ is selected from the group consisting of H, hydroxyl, —OR$^{11}$ and —SR$^{11}$ wherein $R^{11}$ is H, lower alkyl, lower acyl or aryl. Preferably, $R^6$ is H.

X is N, CH or CR$^{12}$ wherein $R^{12}$ is alkyl, aryl, —O-alkyl, —O-aryl, —S-alkyl or —S-aryl, wherein preferred $R^{12}$ moieties are lower alkyl, phenyl, —O-(lower alkyl), —O-phenyl, —S-(lower alkyl) and —S-phenyl. Preferably, X is N, CH or C(lower alkyl), and most preferably, X is N.

R is hydrocarbyl, substituted hydrocarbyl, heteroatom-containing hydrocarbyl or substituted heteroatom-containing hydrocarbyl. In preferred embodiments, R is a five- or six-membered, substituted or unsubstituted, heterocyclic or carbocyclic group. More preferred R groups are five- or six-membered heterocyclic rings having one or more heteroatoms selected from the group consisting of N, O and S, and most preferred R groups are five-membered heterocyclic rings having one to four, optimally one to three, heteroatoms selected from the group consisting of N, O and S.

Suitable R groups, for example, have the structure in which:
c and d represent optional double bonds, and e represents an optional single bond;
m and n are independently 0 or 1, with the proviso that if d is present as a double bond, one of m and n is 0;
one of $R^7$ and $R^8$ is H and the other is H, alkyl, alkenyl, alkynyl, alkoxy, acyl or acyloxy, or one of $R^7$ and $R^8$ is hydroxyl or SR$^{11}$ wherein $R^{11}$ is as defined above, and the other is H, alkyl, alkenyl, alkynyl, acyl, or $R^7$ and $R^8$ together form =O;
Y is N, NH, C or CH, and is optionally bound to $R^1$;
W is O, S, N, N→O or C, with the provisos that (1) if W is O or S, then d is absent and both m and n are 0, and (2) if W is N or N→O, then either (a) d is absent and one but not both of m and n is 0 or (b) d is present and m and n are both 0;
when e is present, Z is N, O, S, CH or CH$_2$, with the proviso that W and Z are not both O and S, and L is CH$_2$, CH$_2$—CH$_2$, CH=CH, NH or NR$^{13}$ where $R^{13}$ is lower alkyl; and
when e is absent, Z is NH, NH$_2$, OH, SH, CH$_2$ or CH$_3$, and L is CH$_3$, CH$_2$CH$_3$, NH$_2$ and NHR$^{13}$.

In preferred compounds, e is present and $R^7$ and $R^8$ are both H, or one of $R^7$ and $R^8$ is H and the other is hydroxyl, lower alkoxy or lower alkynyl, or $R^7$ and $R^8$ together form =O. In particularly preferred compounds, one of $R^7$ and $R^8$ is H and the other is hydroxyl or ethynyl, or $R^7$ and $R^8$ together form =O.

Accordingly, compounds encompassed by structural formula (I) may have the structure of formula (Ia)

(Ia)

wherein:

a, b, c, d, $R^1$ through $R^6$, X and Y are as defined above. When $R^1$ is bound to the substituent R in formula (I), it will be bound to Y in compounds of formula (Ia).

When "e" of compound (Ia) is absent, such structures may be represented by (Ib)

(Ib)

wherein $R^1$ through $R^9$, W, X, Y, a, b, c, d, m and n are as defined with respect to formulae (I) and (Ia), Z is NH, NH$_2$, OH, SH, CH$_2$ or CH$_3$, and L is CH$_3$, CH$_2$CH$_3$, NH$_2$ or NHR$^{13}$. It will be appreciated by those skilled in the art that such compounds are analogs of 15,16-seco steroids, i.e., steroidal compounds in which the covalent bond linking the carbon atoms at the 15 and 16 positions is absent. An alternative acyclic R group, giving rise to analogs of 13,17-seco steroids, has the structural formula wherein W, Y, Z, L, $R^7$, $R^8$, c, d, m and n are as defined previously, although in this embodiment L can be O and it is generally preferred although not essential that Y is O. Examples of such R groups thus include and Those compounds of formula (I) wherein R is carbocyclic may be generally represented by structural formula (Ic)

(Ic)

wherein $R^1$ through $R^8$, X, a, b, c and d are as defined with respect to compounds of formulae (I) and (Ia), Y is C or CH, and L is $CH_2$, $CH_2$—$CH_2$ or CH=CH. When Y is C, then it is covalently bound to $R^1$ and c is present as a double bond. When Y is CH, then either Y is covalently bound to $R^1$ or c is present as a double bond, but not both.

One group of compounds encompassed by the structure of formula (Ia) has the structural formula (II)

(II)

wherein d, $R^2$ through $R^6$ and L are as defined for compounds of formulae (I) and (Ia).

Another group of compounds encompassed by the structure of formula (Ia) has the structural formula (III)

(III)

wherein $R^2$ through $R^6$ and L are as defined for compounds of formulae (I) and (Ia).

An additional group of compounds encompassed by the structure of formula (Ia) has the structural formula (IV)

(IV)

wherein $R^2$ through $R^6$ and L are as defined for compounds of formulae (I) and (Ia).

Another group of compounds encompassed by the structure of formula (Ia) has the structural formula (V)

(V)

wherein c, $R^1$ through $R^6$, and Y are as defined above, Z is N, O, S, CH or $CH_2$, and L is $CH_2$, $CH_2$—$CH_2$, CH=CH, NH or $NR^{13}$.

Additional compounds encompassed by structural formula (I) have the structure of formula (VI)

(VI)

wherein:
c, d, $R^1$ through $R^6$, $R^{11}$ and Y are as defined above for formula (I);

W is C or CH;

Z is N, O, S, CH or CH$_2$; and

L is CH$_2$, CH$_2$—CH$_2$, CH=CH or NH.

The compounds may be in the form of pharmaceutically acceptable salts or esters, or may be modified by appending one or more appropriate functionalities to enhance selected biological properties. Such modifications are known in the art and include those which increase biological penetration into a given biological system, increase oral bioavailability, increase solubility to allow administration by injection, and the like.

Salts of the compounds can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Acid addition salts are prepared from the free base (e.g., compounds having a neutral —NH$_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate and malonate salts.

Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Preparation of esters involves finctionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures.

Certain of the novel compounds are chiral in nature and can thus be in enantiomerically pure form or in a racemic mixture. In some cases, i.e., with regard to certain specific compounds illustrated herein, chirality is indicated. In other cases, it is not, and the invention is intended to encompass both the isomerically pure forms of the compounds shown and the racemic or diastereomeric mixtures thereof.

Pharmaceutical Compositions and Modes of Administration

The pharmaceutical agents of the invention may be conveniently formulated into pharmaceutical compositions composed of one or more of the compounds in association with a pharmaceutically acceptable carrier. See *Remington: The Science and Practice ofpharmacy*, 19th Ed. (Easton, Pa.: Mack Publishing Co., 1995), which discloses typical carriers and conventional methods of preparing pharmaceutical compositions which may be used as described or modified to prepare pharmaceutical formulations containing the compounds of the invention. The compounds may also be administered in the form of pharmaceutically acceptable salts, or as pharmaceutically acceptable esters, as described in the preceding section.

The compounds may be administered orally, parenterally, transdermally, rectally, nasally, buccally, vaginally or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent is combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system, such that a constant level of dosage is maintained. See, e.g., U.S. Pat. No. 3,710,795.

The compounds of the invention may also be administered through the skin or mucosal tissue using conventional transdermal drug delivery systems, wherein the agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferred formulations for vaginal drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

The specific ointment or cream base to be used, as will be appreciated by those skilled in the art, is one that will provide for optimum drug delivery. As with other carriers or vehicles, an ointment base should be inert, stable, nonirritating and nonsensitizing. Also preferred are vaginal suppositories. Suppositories may be formulated using conventional means, e.g., compaction, compression-molding or the like, and will contain carriers suited to vaginal drug delivery, typically a bioerodible material which provides for the desired drug release profile.

Formulations for buccal administration include tablets, lozenges, gels and the like. Alternatively, buccal administration can be effected using a transmucosal delivery system.

Utility

The compounds of the invention find use as chemotherapeutic agents in the treatment of mammals suffering from a wide range of neoplasms, including cancers of the breast, uterus, prostate, colon, lung and the like; the compounds are particularly useful, however, in the treatment of estrogen-dependent cancers such as breast and uterine cancer. A patient in need of treatment is administered an amount of one or more of the above-described compounds which is effective to inhibit the growth of the cancer cell. The dosage requirements will vary with the route of administration, tumor type, the cytotoxic agent and formulation employed, and the particular subject being treated. Generally, however, dosage will be in the range of approximately 0.01 mg/kg/day to 10.0 mg/kg/day, more preferably in the range of about 1.0 mg/kg/day to 5.0 mg/kg/day. The effectiveness of the treatment is monitored by tumor biopsy, radiological methods, or blood enzyme levels, according to standard methods. In addition, the compounds of formula I may be administered in combination with a $5-HT_3$ antagonist, such as ondansetron, granisetron or tropisetron, or other anti-emetic medicaments, for example, a dopamine antagonist such as metoclopramide. Additionally, a compound of formula I may be administered in combination with an anti-inflammatory corticosteroid, such as dexamethasone, or in combination with another chemotherapeutic agent such as cisplatin, dacarbazine (DTIC), dactinomycin, mechlorethamine, streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin and chlorambucil.

The compounds of the invention are additionally useful in treating estrogen-dependent disorders other than estrogen-dependent cancers. Such estrogen-dependent disorders include, for example, endometriosis, benign breast disease, osteoporosis, and the like.

The present compounds are also useful in a method of boron neutron capture therapy (BNCT) for treating cancer, preferably brain gliomas and melanomas or gastrourinary cancers. A patient in need of BNCT is treated with an effective amount of one or more of the present compounds of formula I, and then exposed to thermal neutrons to generate $^7Li$ and $^4He$ thereby causing destruction of tumor cells. The compound administered contains at least a natural abundance, preferably at least about 99%, of boron-10. The preferred effective dose is about 0.1 to about 200 mg/kg of the compound of formula I to body weight of the patient. In addition, the dosage may be pulsed. Typically, the compounds of formula I are administered about 0.5 days to about 30 days before exposure to radiation. The neutron beam must deliver neutrons at the tumor site with an energy distribution sufficient to permit neutron capture by boron-10, generally about 0.4 eV to about 10 keV, as described in U.S.

Pat. No. 5,144,026 to Gabel. The exposure to neutron beam is continued for a time sufficient to effect substantial tumor tissue destruction.

The compounds of the present invention may, in addition, be used as probes in a variety of diagnostic techniques, such as magnetic resonance imaging (MRI), magnetic resonance spectroscopy (MRS) and fluorescence emission spectroscopy. MRI and MRS are noninvasive techniques for detecting and quantitating boron-10 and boron-11, such as in tumor tissue or organ tissue in a patient or in a sample from a patient. A patient is treated with one or more of the compounds of formula I of the present invention. The patient is then placed in an MRI instrument capable of detecting boron. The location and concentration of boron within the patient is then calculated. In the alternative, a sample from the patient is placed in an MRS instrument capable of detecting boron, and the presence and concentration of boron in the sample is determined. In either approach, the method results in an image of the tumor or organ. In fluorescence emission spectroscopy, a fluorescent molecule is irradiated with electromagnetic radiation having a known wavelength, including ultra violet and visible light. The fluorescent molecule absorbs the energy and then emits energy as light having a wavelength longer than the absorbed light. The amount of emitted light is determined by a photodetector. Thus, in the method of the invention, fluorescence emission spectroscopy may be used to detect fluorescence emitted from a fluorescent compound of formula (I).

When used as fluorescent probes in fluorescence emission spectroscopy, the compounds of the present invention are useful in HTS (high throughput screening) of estrogen receptor ligands. For example, estrogen receptor ligands of interest and a fluorescent compound of the invention can be allowed to contact estrogen receptors mounted on a suitable substrate. Only those compounds/ligands having a higher affinity to the estrogen receptor will remain. If, for example, fluorescence emission spectroscopy reveals that a vast majority of the fluorescent compounds of the invention remain bound to the estrogen receptor, it is clear that the estrogen receptor ligands of interest have a relatively lower affinity for the receptor than the fluorescent compound. The opposite conclusion is reached when a small amount of fluorescence is detected. In this way, it is possible to efficiently determine relative estrogen binding affinity of a large number of estrogen receptor ligands.

Synthesis

The compounds of the invention can be synthesized, for example, by the route shown below:

In general, the available 2-formyl-4-methoxybenzeneboronic acid, appropriately substituted on the aromatic ring, serves as the A-ring precursor. The compound is condensed with an appropriate azolyl or cycloalkanyl hydrazine to yield, in a single step, the 3-hydroxyl-protected compound of formula I. Deprotection yields the final product. Compounds of formula (I) wherein $R^1$ is a methylene group can be synthesized by reduction of the lactone before deprotection. In this scheme, the moiety "X" of formulae (I) and (Ia) is N. For compounds wherein X is carbon-containing, e.g., wherein X is CH, a variation on the aforementioned scheme may be used, as follows:

Variations on these basic synthetic schemes to provide other compounds within the scope of the invention will be apparent to those skilled in the art.

EXPERIMENTAL

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

EXAMPLE 1

SCHEME 1

Synthesis of 1,2-dihydro-1,6-dihydroxy-2-(2-carboxyphenyl)-2,3,1-benzodiazaborine lactone (compound 4):

A solution of 2-formyl-4-methoxybenzeneboronic acid (compound 1; 1.8 g, 10 mmol) in 20 mL of absolute ethanol was added to a hot solution of the hydrochloride salt of 2-hydrazinobenzoic acid (compound 2; 2.07 g, 11 mmol) in 10 mL of water. A copious precipitate formed immediately. The mixture was diluted with 50 mL of absolute ethanol and was then suction filtered. After washing with a small amount of absolute ethanol and drying in vacuo, 1.77 g (64%) of the methoxy precursor 3 was obtained, mp 240–242° C. (ethanol). $^1$H NMR (CDCl$_3$) δ 8.39 (s, 1, H4), 8.38 (bs, 1), 8.34 (d, J=5.4 Hz, 1), 8.31 (pseudo-t, 2), 7.80 (pseudo-t, 1), 7.37 (d of d, 1), 7.33 (d of d, 1), 7.21 (d, J=2.3 Hz, 1), 3.97 (s, 3, OCH$_3$). Low-resolution DCI mass spectrum, m/z 279 (100%, MH$^+$). Exposure of this to BBr$_3$ in CH$_2$Cl$_2$ solution at 23° C. overnight effected the removal of the phenolic protecting group and gave 4: $^1$H NMR ((CD$_3$)$_2$SO) δ 10.52 (s, 1, PhOH), 8.53 (s, 1, H4), 8.26 (d, 1), 8.12 (d, 1), 8.08 (d, 1), 8.86 (pseudo-t, 1), 7.47 (pseudo-t, 1), 7.29 (s, 1), 7.27 (d, 1). Low-resolution DCI mass spectrum, m/z 265 (100%, MH$^+$).

EXAMPLE 2

SCHEME 2

Synthesis of 1,2-dihydro-1,6-dihydroxy-2-[2-(hydroxymethyl)phenyl]-2,3,1-benzodiazaborine anhydride (compound 6):

A solution of 3 (556 mg, 2 mmol) in 35 mL of anhydrous THF under argon was treated with solid LiBH$_4$ (200 mg, excess) and the reduction mixture was stirred at 23° C. for 24 h. After adding 2 mL of EtOAc to quench excess borohydride, the mixture was treated with water and was extracted several times with CH$_2$Cl$_2$. The combined organic layers were dried (Na$_2$SO$_4$) and then were rotary evaporated to a residue which proved to be a binary mixture by TLC (CH$_2$Cl$_2$ as eluent). Elution of a CH$_2$Cl$_2$ solution of this mixture through a short SiO$_2$ column afforded a small sample of the methoxy precursor, compound 5, mp 122–124° C. (EtOH). $^1$H NMR (CDCl$_3$) δ 8.10 (s, 1, H4), 8.01 (d, J=8.5 Hz, 1), 7.93 (d, J=8.3 Hz, 1), 7.35 (d of d, 1), 7.32 (pseudo-t, 1), 7.19 (d of d, J=2.6, 8.4 Hz, 1), 7.09 (d, J=2.4 Hz, 1), 7.05 (bs, 1), 5.32 (s, 2, CH$_2$), 3.93 (s, 3, OCH$_3$). Low-resolution DCI mass spectrum, m/z 265 (100%, MH$^+$). Exposure of this to BBr$_3$ effected the removal of the phenolic protecting group, giving 6: $^1$H NMR (CDCl$_3$) δ 8.05 (s, 1), 8.01 (d, J=8.1 Hz, 1), 7.93 (d, J=8.0 Hz, 1), 7.34 (dt, 2), 7.06 (m, 3), 5 (s, 2, CH$_2$). Low resolution thermospray mass spectrum, m/z 251 (100%, MH$^+$).

EXAMPLE 3

SCHEME 3

Synthesis of 1,2-dihydro-1,6-dihydroxy-2-(imidazolidinyl)-2,3,1-benzodiazaborine (compound 8):

A solution of 1 (450 mg, 2.5 mmol) and 2-hydrazinoimidazoline hydrobromide (compound 7, 500 mg, 2.75 mmol) in 7.5 mL of absolute ethanol was treated with a solution of 100 mg of NaOH in 1.5 miL of water. The suspension of the precipitate generated was stirred at 23° C. for 24 h, after which the mixture was suction filtered and the solid washed with a small amount of ethanol. Drying in vacuo afforded 470 mg (77%) of 8 as a white microcrystalline anhydrous dimer: mp 281–282° C. (ethanol). $^1$H NMR ((CD$_3$)$_2$SO) δ 7.57 (s, 1, exchanges upon addition of D$_2$O, OH), 7.49 (s, 1, H4), 7.38 (d, 1), 6.96 (s, 1), 6.94 (d, 1), 3.78 (s, 3, OCH$_3$), 3.32 (t, 1), 3.26 (t, 1), 2.97 (pseudo-q, 1), 2.73 (pseudo-q, 1). Low-resolution DCI mass spectrum, m/z 471 (100%, anhydrous dimer MH$^+$).

EXAMPLE 4

SCHEME 4

Synthesis of 1,2-dihydro-1,6-dihydroxy-2-(6-pyridinyl)-2,3,1 -benzodiazaborine (compound 11 in Scheme 4):

A solution of 1 (450 mg, 2.5 mmol) in 2.5 mL of absolute ethanol was treated with a solution of 2-hydrazinopyridine (compound 9; 300 mg, 2.75 mmol) in 2.5 mL of ethanol, and the reaction mixture was allowed to stand at 23° C. overnight. The precipitate that formed was collected by suction filtration, washed with a small amount of ethanol, and was dried in vacuo, giving 400 mg (63%) of the methoxy precursor 10 as a white microcrystalline anhydrous dimer: compound 10, mp 256–258.5° C. (EtOH). $^1$H NMR ((CD$_3$)$_2$SO) δ 7.92 (s, 1, H4), 7.86 (d, 1), 7.71 (pseudo-t, 1), 7.43 (d, J=8.2 Hz, 1), 7.20 (s, 1), 7.02 (d of d, 1), 6.87 (d, 1), 6.64 (pseudo-t, 1), 3.85 (s, 3, OCH$_3$). Low-resolution DCI mass spectrum, m/z 489 (61%, anhydrous dimer MH$^+$), 254 (100%, MH$^+$). Exposure of this to BBr$_3$ effected the removal of the phenolic protecting group, giving 11: $^1$H NMR ((CD$_3$)$_2$SO) d 10.5 (s, 1, OH), 9.55 (s, 1, OH), 7.83 (m, 2), 7.70 (dt, J=7.2, 1.8 Hz, 1), 7.32 (d, J=8.0 Hz, 1), 6.96 (d, J=2.0 Hz, 1), 6.88 (d, J=1.4 Hz, 1), 6.86 (s, 1), 6.34 (pseudo-t, J=6.6 Hz, 1). Low-resolution DCI mass spectrum, m/z 240 (100%, MH$^+$).

EXAMPLE 5

SCHEME 5

Figure 1:
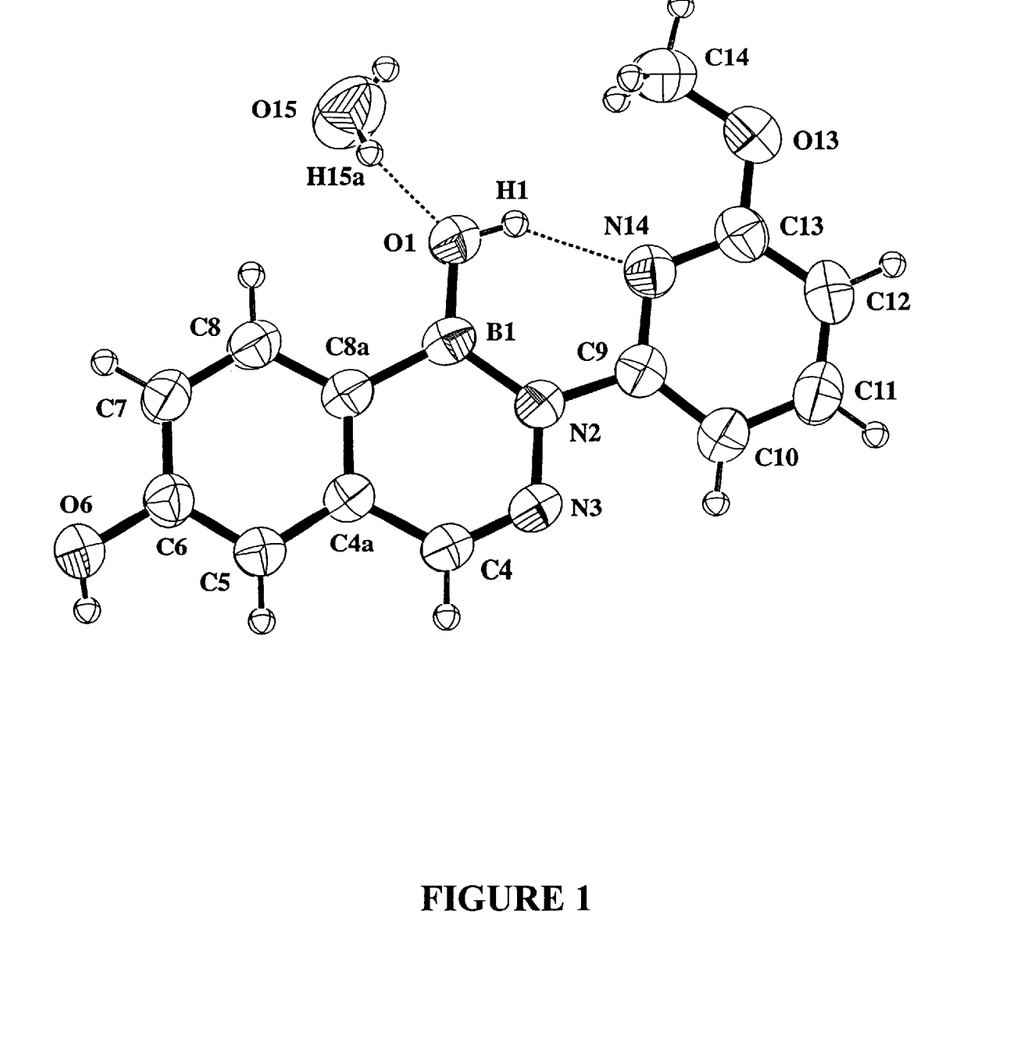
FIG. 1 shows the crystal structure of a compound of the invention, synthesized and characterized as described in Example 5.

Synthesis of 1,2-dihydro-1,6-dihydroxy-2-(2-methoxy-6-pyridinyl)-2,3,1-benzodiazaborine (compound 15):

A mixture of 2-chloro-6-methoxypyridine (compound 12; 2.87 g, 20 mmol) and anhydrous hydrazine (11 mL, excess) was heated under argon on a steam bath overnight. The mixture was allowed to cool to 23° C. and then was extracted with Et$_2$O (10×10 mL). The combined ether extracts were rotary evaporated to afford 1.58 g (57%) of 2-hydrazino-6-methoxypyridine 13 as a yellow liquid that was ~95% pure by NMR: $^1$H NMR (CDCl$_3$) δ 7.38 (pseudo-t, 1), 6.20 (d, J =8.0 Hz, 1), 6.09 (d, J=8.0 Hz, 1), 5.71 (bs, 1, exchanges upon addition of D$_2$O, NH), 3.84 (s, 3, OCH$_3$), 3.1 (bs, 2, exchanges upon addition of D$_2$O, NH$_2$). A solution of this hydrazine (1.58 g, 11 mmol) in 10 mL of absolute ethanol was combined with a solution of 1 (1.8 g, 10 mmol) in 20 mL of absolute ethanol, and the reaction mixture produced a precipitate within several minutes. The mixture was allowed to stand at 23° C. overnight. The solid was collected by suction filtration, washed with a small amount of ethanol, and was dried in vacuo, giving 1.65 g of the methoxy precursor 14. An additional 510 mg of this precipitated from the filtrate after it had been concentrated on a rotary evaporator to a small volume. Combined yield: 2.15 g (76%): mp 161–162° C. (ethanol). $^1$H NMR ((CD$_3$)$_2$SO) δ 10.45 (s, 1, exchanges upon addition of D$_2$O, OH), 8.25 (s, 1, H4), 8.04 (d, J=8.2 Hz, 1), 7.88 (pseudo-t, 1), 7.54 (d,J=8.2 Hz, 1), 7.36 (s, 1), 7.26 (d, J=8.25 Hz, 1), 6.68 (d, J=7.9 Hz, 1), 6.64 (pseudo-t 1), 3.92 (s, 3, OCH$_3$), 3.90 (s, 3, OCH$_3$). Low-resolution DCI mass spectrum, m/z 284 (100%, MH$^+$). Exposure of this compound to molten C$_5$H$_5$N.HCl for 10 min effected removal of the hydroxy pyridine protecting group only, by $^1$H NMR. Exposure to BBr$_3$ in CH$_2$Cl$_2$ solution at 23° C. overnight effected the removal of the phenolic protecting group only, giving 15: mp 198–199° C. (ethanol). $^1$H NMR ((CD$_3$)$_2$SO) δ 8.17 (s, 1, H4), 7.98 (d, 1), 7.88 (pseudo-t, 1), 7.54 (d, 1), 7.12 (m, 3), 6.67 (d, 1), 3.92 (s, 3, OCH$_3$). Low-resolution DCI mass spectrum, m/z 270 (100%, MH$^+$). X-ray quality crystals of 15 were grown from absolute ethanol and a crystal structure determination was made; the crystal structure of the compound is shown in FIG. 1. Robinson et al. (1999), "A Boron-Containing Estrogen Mimic," J. Act Crystallogr. C55:1701–1704.

EXAMPLE 6

SCHEME 6

Synthesis of 2-[(4-chlorobenzyl)-3,5-dihydroimidazol-4-on-2-yl]-1,2-dihydro-1-hydroxy-6-methoxy-2,3,1-benzodiazaborine (compound 17):

A mixture of 1 (360 mg, 2.0 mmol) and 3-(4-chlorobenzyl)-2-hydrazino-3,5-dihydroimidazol-4-one (compound 16, commercially available from Maybridge Chemical Co., Ltd., Ryan Scientific #RF03409; 500 mg, 2.1 mmol) in 6 mL of absolute ethanol was treated with 1 drop of AcOH and was warmed on a steam bath until homogeneous. The mixture was allowed to stand at 23 ° C. overnight, whereupon the 137 mg of the starting hydrazine that had separated as crystals (mp 186–188° C.) was removed by suction filtration. The filtrate was rotary evaporated to dryness, and the residue was triturated with Et$_2$O to give 528 mg (69%, 91% based on unrecovered hydrazine) of the methoxy precursor (compound 17) as a pale yellow powder: mp 135–145° C. (EtOH). $^1$H NMR ((CD$_3$)$_2$SO) δ 9.16 (s, exchanges with D$_2$O, 1, OH), 7.62 (d, J=8.4 Hz, 1), 7.40 (d, J =8.5 Hz, 2, p-ClCA), 7.32 (d, J=8.5 Hz, 2, p-ClC$_6$H$_4$), 7.12 (m, 3), 6.97 (d, J=8.0 Hz, 1), 6.85 (d, J =8.0 Hz, 1), 6.68 (s, 1), 4.23 (d, J=5.6 Hz, 2, benzyl-CH$_2$), 3.67 (s, 3, OCH$_3$). Low-resolution DCI mass spectrum, m/z 383 (2%, MH$^+$). Deprotection of 17 can be effected using conventional techniques to form 18.

EXAMPLE 7

SCHEME 7

Synthesis of 1,2-dihydro-1,6-dihydroxy-2-[(4H)-1,2,4-triazole-3-thiol-4-yl]-2,3,1-benzodiazaborine (compound 21):

A mixture of 1 (675 mg, 3.75 mmol) and 5-hydrazino-4H-1,2,4-triazole-3-thiol (compound 19, commercially available from Sigma-Aldrich Library of Rare Chemicals, #S98701-8; 500 mg, 3.8 mmol) in 40 mL of hot absolute ethanol was treated with 1 drop of AcOH. The suspension was allowed to stand at 23 °C. overnight, and then was suction filtered to give 520 mg (50%) of the methoxy precursor (compound 20) as a white powder: mp 245–260 °C. slow dec.). $^1$H NMR ((CD$_3$)$_2$SO) δ 8.21 (s, 1), 8.20 (d, 1), 7.40 (s, 1), 7.31 (dd, 1), 3.90 (s, 3, OCH$_3$). Low-resolution DCI mass spectrum, m/z 276 (100%, MH$^+$), 250 (M−BO+2H$^+$). Deprotection of 20 can be effected using conventional techniques to form 21.

EXAMPLE 8

SCHEME 8

1,2-Dihydro-1,6-dihydroxy-2-(I-oxo-3-pyridazinyl)-2,3,1-benzodiazaborine (compound 25):

Following a procedure of Pollak et al. (1968) *J. Heterocycl. Chem.* 5: 513–516, a mixture of 3-methoxypyridazine 1-oxide (compound 22, commercially available, see Specs and BioSpecs #CIF5046; 660 mg, 5.23 mmol) and anhydrous hydrazine (3.3 mL, excess) in 1.5 mL of iPrOH was heated at reflux under argon for 2 hours and then was kept at 23 °C. overnight. The mixture was rotary evaporated in vacuo and the crude 3-hydrazino-pyridazine 1-oxide (compound 23) [$^1$H NMR ((CD$_3$)$_2$SO) δ 8.22 (bs, 1), 7.59 (d, J=5.3 Hz, 1), 7.44 (m, 1), 6.62 (d,J=8.5 Hz, 1)] was directly condensed with 1 (1.0 g, 5.6 mmol) first in 10 mL and then in 60 mL of absolute ethanol on a steam bath for 30 minutes. The mixture was allowed to stand at 4 °C. overnight, and then the solid was collected by suction filtration, washed with a small amount of cold ethanol, and dried in vacuo to give 750 mg (53%) of the methoxy precursor 24: mp, 229–232° C. $^1$H NMR ((CD$_3$)$_2$SO) δ 9.09 (s, 1, exchanges upon addition of D$_2$O, OH), 8.29 (s, 1, H4), 8.27 (d,J=6.1 Hz, 1), 8.15 (d, J=8.3 Hz, 1), 7.99 (dd, J=8.6, 6.1 Hz, 1), 7.68 (d, J=8.7 Hz, 1), 7.40 (d,J=2.1 Hz, 1), 7.30 (dd, J=8.4, 2.2 Hz, 1). Low-resolution DCI mass spectrum, m/z 271 (100%, MH$^+$). Deprotection of 24 can be effected using conventional techniques to form 25.

EXAMPLE 9

Antiproliferative Assay Procedure

MCF-7 cells were obtained from the American Type Culture Collection (ATCC, Rockville, Md.). Exponentially growing cells were plated (96-well plates) in MEM (minimal essential medium) containing NaHCO$_3$, CCD (charcoal-coated dextran)-stripped 10% FCS (fetal calf serum), and glycine. Cultures were incubated at 37° C. for 1 day, then treated with target by replacing the medium with 100 μL MEM containing supplements and target (3 wells at each of 5 concentrations). The relative effect of each concentration was compared to that of β-estradiol (positive control) by the alamar Blue™ assay (Biosource International), in which the dye is reduced by cellular mitochondrial enzymes to a soluble fluorophore with an intensity directly proportional to cell number. After cultures were incubated with target, alamar Blue™ diluted to 20% in MEM was added (100 μL/well) and cells were incubated for about 4 h, until a color change indicated sufficient amounts of reduced dye for quantitation. Relative cell number was evaluated directly from the plates by fluorimetry (560 nm excitation, 590 nm detection) on a Millipore 2300 CytoFluor. The concentration at which 50% effectiveness is seen (EC$_{50}$) was calculated from statistically significant, reproducible effects. Statistical analysis was performed using JMP software (SAS Institute). Results are set forth in Table 1:

TABLE 1

| Compound | Concentration | % Inhibition |
| --- | --- | --- |
| 4 | $10^{-9}$ | 0 |
| 4 | $10^{-8}$ | 6 |
| 4 | $10^{-7}$ | 2 |
| 4 | $10^{-6}$ | 4 |
| 4 | $10^{-5}$ | 13 |
| 11 | $10^{-9}$ | 5 |
| 11 | $10^{-8}$ | 8 |
| 11 | $10^{-7}$ | 8 |
| 11 | $10^{-6}$ | 10 |
| 11 | $10^{-5}$ | 55 |
| 15 | $10^{-9}$ | 0 |
| 15 | $10^{-8}$ | 0 |
| 15 | $10^{-7}$ | 0 |
| 15 | $10^{-6}$ | 3 |
| 15 | $10^{-5}$ | 62 |
| tamoxifen | $10^{-9}$ | 0 |
| tamoxifen | $10^{-8}$ | 5 |
| tamoxifen | $10^{-7}$ | 29 |
| tamoxifen | $10^{-6}$ | 54 |
| tamoxifen | $10^{-5}$ | 95 |

What is claimed is:

1. A compound having the structural formula (I)

(I)

wherein:

a and b represent optional double bonds;

$R^1$ is H, carbonyl, methylene or mono(lower alkyl)-substituted methylene, wherein, when carbonyl, methylene or mono(lower alkyl)-substituted methylene, $R^1$ is covalently bound to an atom contained within R;

$R^2$ is selected from the group consisting of H, lower alkyl, lower acyl, phenyl, benzyl, —C(O)-aryl and —$SO_2NH_2$;

$R^3$ is H or lower alkyl;

$R^4$ is selected from the group consisting of H, methoxy, halogen, cyano, —$CH_2CH=CH_2$, —CHO, —$NR^9R^{10}$ and —$(CH_2)NR^9R^{10}$ wherein $R^9$ and $R^{10}$ are independently H or lower alkyl;

$R^5$ is selected from the group consisting of H, halogen, —$NO_2$, —CHO, —$CH_2CH=CH_2$, —$NR^9R^{10}$ and —$(CH_2)NR^9R^{10}$ wherein $R^9$ and $R^{10}$ are independently H or lower alkyl;

$R^6$ is selected from the group consisting of H, hydroxyl, —$OR^{11}$ and —$SR^{11}$ wherein $R^{11}$ is H, lower alkyl, lower acyl or aryl;

R is a five- or six-membered, substituted or unsubstituted heterocyclic group;

X is N, CH or $CR^{12}$ wherein $R^{12}$ is alkyl, aryl, —O-alkyl, —O-aryl, —S-alkyl or —S-aryl;

and pharmaceutically acceptable salts and esters thereof.

2. The compound of claim 1, wherein:

$R^1$ is H or methylene;

$R^2$, $R^4$, $R^5$ and $R^6$ are H; and $R^3$ is H or lower alkyl.

3. The compound of claim 1, wherein a and b both represent double bonds.

4. The compound of claim 2, wherein a and b both represent double bonds.

5. The compound of claim 4, wherein X is N.

6. The compound of claim 4, wherein X is CH.

7. The compound of claim 1, wherein R contains one to four atoms selected from the group consisting of N, O and S.

8. A compound having the structural formula (Ic)

(Ic)

wherein:

a, b, c and d represent optional double bonds;

m and n are independently 0 or 1, with the proviso that if d is present as a double bond, one of m and n is 0;

$R^1$ is H, methylene or mono(lower alkyl)-substituted methylene, wherein, when methylene or mono(lower alkyl)-substituted methylene, $R^1$ is directly and covalently bound to Y;

$R^2$ is selected from the group consisting of H, lower alkyl, lower acyl, phenyl, benzyl, —C(O)-aryl and —$SO_2NH_2$;

$R^3$ is H or lower alkyl;

$R^4$ is selected from the group consisting of H, methoxy, halogen, cyano, —$CH_2CH=CH_2$, —CHO, —$NR^9R^{10}$ and —$(CH_2)NR^9R^{10}$ wherein $R^9$ and $R^{10}$ are independently H or lower alkyl;

$R^5$ is selected from the group consisting of H, halogen, —$NO_2$, —CHO, —$CH_2CH=CH_2$, —$NR^9R^{10}$ and —$(CH_2)NR^9R^{10}$ wherein $R^9$ and $R^{10}$ are independently H or lower alkyl;

$R^6$ is selected from the group consisting of H, hydroxyl, —$OR^{11}$ and —$SR^{11}$ wherein $R^{11}$ is lower alkyl, lower acyl or aryl;

one of $R^7$ and $R^8$ is H and the other is H, alkyl, alkenyl, alkynyl, alkoxy, acyl or acyloxy, or one of $R^7$ and $R^8$ is hydroxyl and the other is H, alkyl, alkenyl, alkynyl, acyl, or $R^7$ and $R^8$ together form =O;

X is CH or $CR^{12}$ wherein $R^{12}$ is alkyl, aryl, —O-alkyl, —O-aryl, —S-alkyl or —S-aryl;

Y is C or CH, and is optionally bound directly and covalently to $R^1$; and

L is $CH_2$, $CH_2$—$CH_2$, or CH=CH;

and pharmaceutically acceptable salts and esters thereof.

9. The compound of claim 8, wherein a and b both represent double bonds.

10. The compound of claim 9, wherein:

$R^1$ is H or methylene;

$R^2$, $R^4$, $R^5$ and $R^6$ are H;

$R^3$ is H or lower alkyl; and one of $R^7$ and $R^8$ is H and the other is H, hydroxyl, lower alkoxy or lower alkynyl, or $R^7$ and $R^8$ together form =O.

11. The compound of claim 10, wherein $R^1$ is H, $R^3$ is H, and one of $R^7$ and $R^8$ is H and the other is hydroxyl or ethynyl, or $R^7$ and $R^8$ together form =O.

12. A compound having the structural formula (I)

(I)

wherein:

a and b represent optional double bonds;

$R^1$ is H, carbonyl, methylene or mono(lower alkyl)-substituted methylene, wherein, when carbonyl, methylene or mono(lower alkyl)-substituted methylene, $R^1$ is covalently bound to an atom contained within R;

$R^2$ is selected from the group consisting of H, lower alkyl, lower acyl, phenyl, benzyl, —C(O)-aryl and —SO$_2$NH$_2$;

$R^3$ is H or lower alkyl;

$R^4$ is selected from the group consisting of H, methoxy, halogen, cyano, —CH$_2$CH=CH$_2$, —CHO, —NR$^9$R$^{10}$ and —(CH$_2$)NR$^9$R$^{10}$ wherein $R^9$ and $R^{10}$ are independently H or lower alkyl;

$R^5$ is selected from the group consisting of H, halogen, —NO$_2$, —CHO, —CH$_2$CH=CH$_2$, —NR$^9$R$^{10}$ and —(CH$_2$)NR$^9$R$^{10}$ wherein $R^9$ and $R^{10}$ are independently H or lower alkyl;

$R^6$ is selected from the group consisting of H, hydroxyl, —OR$^{11}$ and —SR$^{11}$ wherein $R^{11}$ is H, lower alkyl, lower acyl or aryl;

R is an acyclic, optionally substituted hydrocarbyl or heteroatom-containing hydrocarbyl group;

X is N, CH or CR$^{12}$ wherein $R^{12}$ is alkyl, aryl, —O-alkyl, —O-aryl, —S-alkyl or —S-aryl;

and pharmaceutically acceptable salts and esters thereof.

13. The compound of claim 12, wherein:

$R^1$ is H or methylene;

$R^2$, $R^4$, $R^5$ and $R^6$ are H; and $R^3$ is H or lower alkyl.

14. The compound of claim 12, wherein a and b both represent double bonds.

15. The compound of claim 13, wherein a and b both represent double bonds.

16. The compound of claim 15, wherein X is N.

17. The compound of claim 15, wherein X is CH.

18. A pharmaceutical composition comprising a therapeutically effective amount of the compound of claim 1 in combination with a pharmaceutically acceptable carrier.

19. A pharmaceutical composition comprising a therapeutically effective amount of the compound of claim 8 in combination with a pharmaceutically acceptable carrier.

20. A pharmaceutical composition comprising a therapeutically effective amount of the compound of claim 12 in combination with a pharmaceutically acceptable carrier.

21. The pharmaceutical composition of claim 18, in unit dosage form.

22. The pharmaceutical composition of claim 21, wherein the pharmaceutically acceptable carrier is suitable for oral drug administration.

23. A method for treating an individual with an estrogen-dependent disorder, comprising administering to the individual a therapeutically effective amount of the compound of claim 1.

24. A method for treating an individual with an estrogen-dependent disorder, comprising administering to the individual a therapeutically effective amount of the compound of claim 8.

25. A method for treating an individual with an estrogen-dependent disorder, comprising administering to the individual a therapeutically effective amount of the compound of claim 12.

26. The method of claim 23, wherein the estrogen-dependent disorder is breast cancer.

27. A method for detecting tumor cells in a mammalian individual, comprising administering to the individual an effective tumor-detecting amount of the compound of claim 1; and detecting any of said compound associated with and retained by tumor cells present in the mammalian individual.

28. The method of claim 27, wherein the detecting is carried out using $^{11}$B magnetic resonance spectroscopy.

29. The method of claim 27, wherein the detecting is carried out using $^{11}$B magnetic resonance imaging.

30. A method for detecting tumor cells in a mammalian individual, comprising administering to the individual an effective tumor-detecting amount of the compound of claim 1; and detecting any of said compound associated with and retained by tumor cells present in the mammalian individual using fluorescence emission spectroscopy.

31. A method for detecting tumor cells in a mammalian individual, comprising administering to the individual an effective tumor-detecting amount of the compound of claim 8; and detecting any of said compound associated with and retained by tumor cells present in the mammalian individual using fluorescence emission spectroscopy.

32. A method for detecting tumor cells in a mammalian individual, comprising administering to the individual an effective tumor-detecting amount of the compound of claim 12 wherein $R^1$ is carbonyl or methylene; and detecting any of said compound associated with and retained by tumor cells present in the mammalian individual using fluorescence emission spectroscopy.

33. A method for performing boron neutron capture therapy, comprising: administering to a patient an effective amount of the compound of claim 1; locating a cancerous tumor in the individual by scanning the patient with a device capable of detecting the location and extent of boron uptake within the patient's body; irradiating the tumor so located with thermal neutrons to permit neutron capture by $^{10}$B, the decay of which into $^7$Li and $^4$He causes destruction of tumor cells.

34. A method for imaging organ tissue in a mammalian individual, comprising administering to the individual an effective organ-imaging amount of the compound of claim 1, and detecting any of said compound associated with and retained by organ tissue present in the mammalian individual.

35. A method for imaging organ tissue in a mammalian individual, comprising administering to the individual an effective organ-imaging amount of the compound of claim 8, and detecting any of said compound associated with and retained by organ tissue present in the mammalian individual.

36. A method for imaging organ tissue in a mammalian individual, comprising administering to the individual an effective organ-imaging amount of the compound of claim 12, and detecting any of said compound associated with and retained by organ tissue present in the mammalian individual.

* * * * *